(12) United States Patent
Baynham et al.

(10) Patent No.: US 7,850,733 B2
(45) Date of Patent: Dec. 14, 2010

(54) PLIF OPPOSING WEDGE RAMP

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 900 days.

(21) Appl. No.: 11/741,274

(22) Filed: Apr. 27, 2007

(65) Prior Publication Data

US 2007/0270968 A1 Nov. 22, 2007

Related U.S. Application Data

(63) Continuation of application No. 10/776,663, filed on Feb. 10, 2004, now Pat. No. 7,211,112.

(51) Int. Cl.
*A61F 2/44* (2006.01)
(52) U.S. Cl. .................. 623/17.11; 623/17.15
(58) Field of Classification Search ... 623/17.11–17.16; 606/246, 247, 90
See application file for complete search history.

(56) References Cited

U.S. PATENT DOCUMENTS

| | | | |
|---|---|---|---|
| 5,609,635 A | 3/1997 | Michelson | |
| 5,658,335 A | 8/1997 | Allen | |
| 5,665,122 A | 9/1997 | Kambink | |
| 5,865,848 A * | 2/1999 | Baker | 623/17.15 |
| 6,015,436 A | 1/2000 | Schonhoffer | |
| 6,102,950 A * | 8/2000 | Vaccaro | 623/17.16 |
| 6,120,506 A | 9/2000 | Kohrs et al. | |
| 6,443,989 B1 | 9/2002 | Jackson | |
| 6,454,807 B1 * | 9/2002 | Jackson | 623/17.15 |
| 6,562,074 B2 | 5/2003 | Gerbec et al. | |
| 6,706,070 B1 | 3/2004 | Wagner et al. | |
| 6,733,535 B2 | 5/2004 | Michelson | |
| 6,852,129 B2 * | 2/2005 | Gerbec et al. | 623/17.15 |
| 7,094,237 B2 | 8/2006 | Gradel | |
| 7,211,112 B2 | 5/2007 | Baynham | |
| 7,637,952 B2 * | 12/2009 | Landry et al. | 623/17.11 |
| 2002/0068976 A1 | 6/2002 | Jackson | |
| 2004/0087947 A1 | 5/2004 | Lim et al. | |
| 2005/0010216 A1 | 1/2005 | Gradel | |
| 2005/0177235 A1 | 8/2005 | Baynham | |
| 2006/0064166 A1 | 3/2006 | Zucherman | |
| 2007/0270968 A1 | 11/2007 | Baynham | |

* cited by examiner

*Primary Examiner*—Pedro Philogene
(74) *Attorney, Agent, or Firm*—McHale & Slavin, P.A.

(57) ABSTRACT

A spinal fusion implant for implantation between adjacent vertebrae is formed in the approximate shape of a hollow cube. The device has an upper section and a lower section separated by a distractor all of which are relatively movable. The sidewalls of the upper section and the lower section terminate in inclined planes so that the sections move away from each other as the wedge shaped distractor increases the height of the device.

12 Claims, 6 Drawing Sheets

PLIF OPPOSING WEDGE RAMP

RELATED APPLICATIONS

This application is a continuation in part of U.S. patent application Ser. No. 10/776,663 filed Feb. 10, 2004 now U.S. Pat. No. 7,211,112.

BACKGROUND OF THE INVENTION

1. Field of the Invention

This invention relates to the field of orthopedic surgery and, more particularly, to implants to be placed between vertebrae in the spine.

2. Background of the Invention

Spinal stabilization is one approach to alleviating chronic back pain caused by displaced disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to or, in place of, the bone graft material, a spinal implant may be inserted in the intervertebral space.

The conventional surgical approach for stabilization has been posteriorly for ease of access to the spine and to avoid interfering with internal organs and tissue. Usually the implant site is prepared to maintain natural lordosis and to accept a certain sized implant within certain pressure limits. This requires considerable time and skill by the surgeon.

DESCRIPTION OF THE PRIOR ART

U.S. Pat. No. 6,562,074 to Gerber et al issued May 13, 2003 discloses a spinal insert which can be manipulated to adjust the height of the implant through links connected to the upper and lower plates.

U.S. Pat. No. 6,120,506 issued Sep. 19, 2000 to Kohrs et al discloses a lordotic implant and a tap for use in preparing the vertebrae. The implant is designed to be inserted between the non-parallel end plates of adjacent vertebrae and maintain the natural lordotic angle of the spine. This is done through the use of a threaded tapered plug inserted in a tapped hole in the direction required by the lordosis of the spine. The implant is hollow and has radial apertures for accommodating bone graft material.

U.S. Pat. No. 6,015,436 issued Jan. 18, 2000 to Shoenhoeffer discloses a tubular spinal implant. The implant is hollow and has radial apertures for interbody fusion through bone growth material. The device is placed between adjacent vertebrae with the opposite ends of the tube contacting the opposing vertebrae. The opposite ends are threaded together to form the hollow tube.

SUMMARY OF THE INVENTION

The implant of this invention has a main body having upper and a lower sections with mating sidewalls relatively movable along an inclined ramp. The inclined ramp forms a wedge movable between inclined sidewalls of the main body sections. The main body sections and the inclined ramp form a hollow cube-shaped structure with common open sides. The implant is inserted in an extended thin mode between adjacent vertebrae and the ramp is inserted between the sections through one end. The body sections are connected at the other end by a link which permits the sections to move vertically away from each other for increasing the height of the implant and engaging the opposing surfaces of adjacent vertebrae. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion allowing the implant to be inserted through a small incision and increased in size in situ.

It is another objective of the instant invention to teach a spinal implant which allows the surgeon to provide for lordosis intraoperatively and to distract through the implant.

It is a further objective of the instant invention to teach a spinal implant having increased contact area in the disk space.

It is yet another objective of the instant invention to teach an implant facilitating interbody fusion through bone graft or an ingrowth-type implant.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
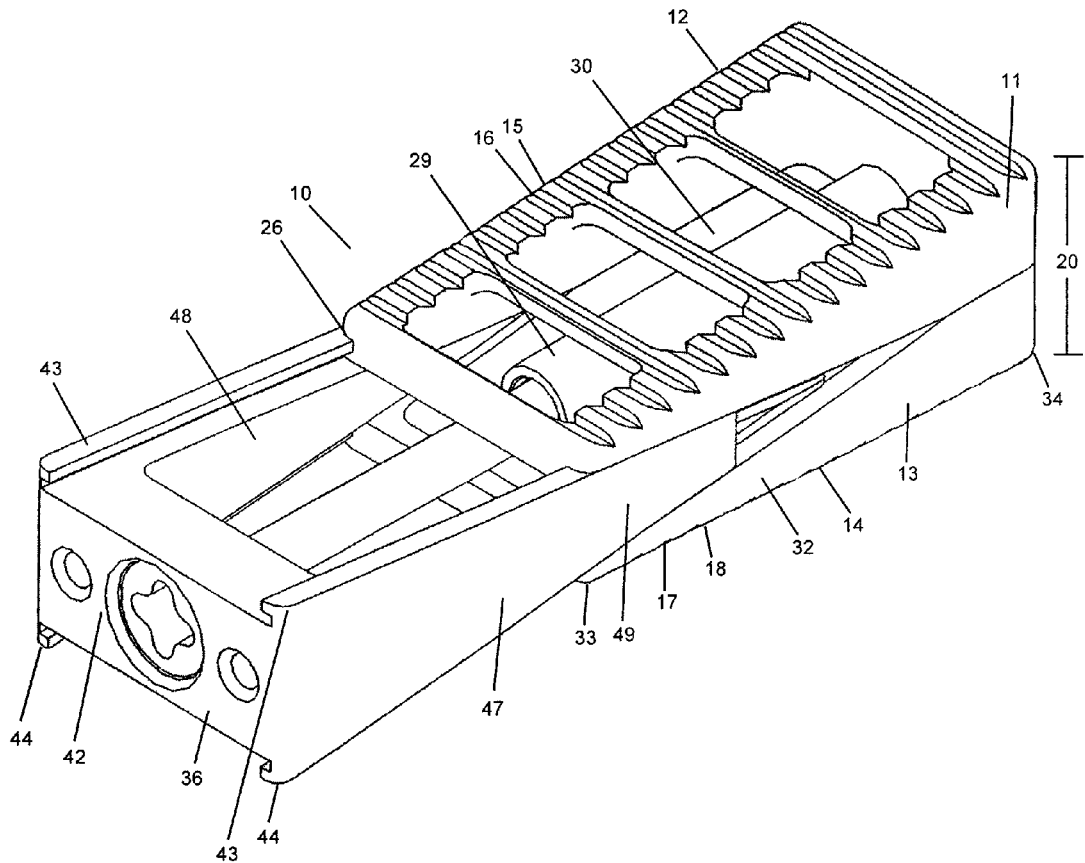
FIG. 1 is a perspective of the spinal fusion implant of this invention in the thin mode.

The spinal fusion device 10 is inserted in the intervertebral space in the insertion mode, shown in FIG. 1, to replace damaged, missing or excised disk material. This extended position allows the leading end of the implant to be inserted in a small intervertebral space without the necessity of excising structurally sound bone. The upper section 11 has a top surface 12 for engaging the end plate of a vertebra and the lower section 13 has a bottom surface 14 for engaging the end plate of an adjacent vertebra. The top surface 12 and the bottom surface 14 are planar to provide a large contact area with each vertebra. Each contact surface has a roughened finish to provide better purchase on the end plates of the vertebrae. As shown, the top and bottom surfaces have a series of lands and grooves 15, 16, 17 and 18 though other stippled treatment may be employed. Of course, the device may be rotated about its longitudinal axis 180 degrees so that the upper section becomes the lower section and vice versa.

Figure 2:
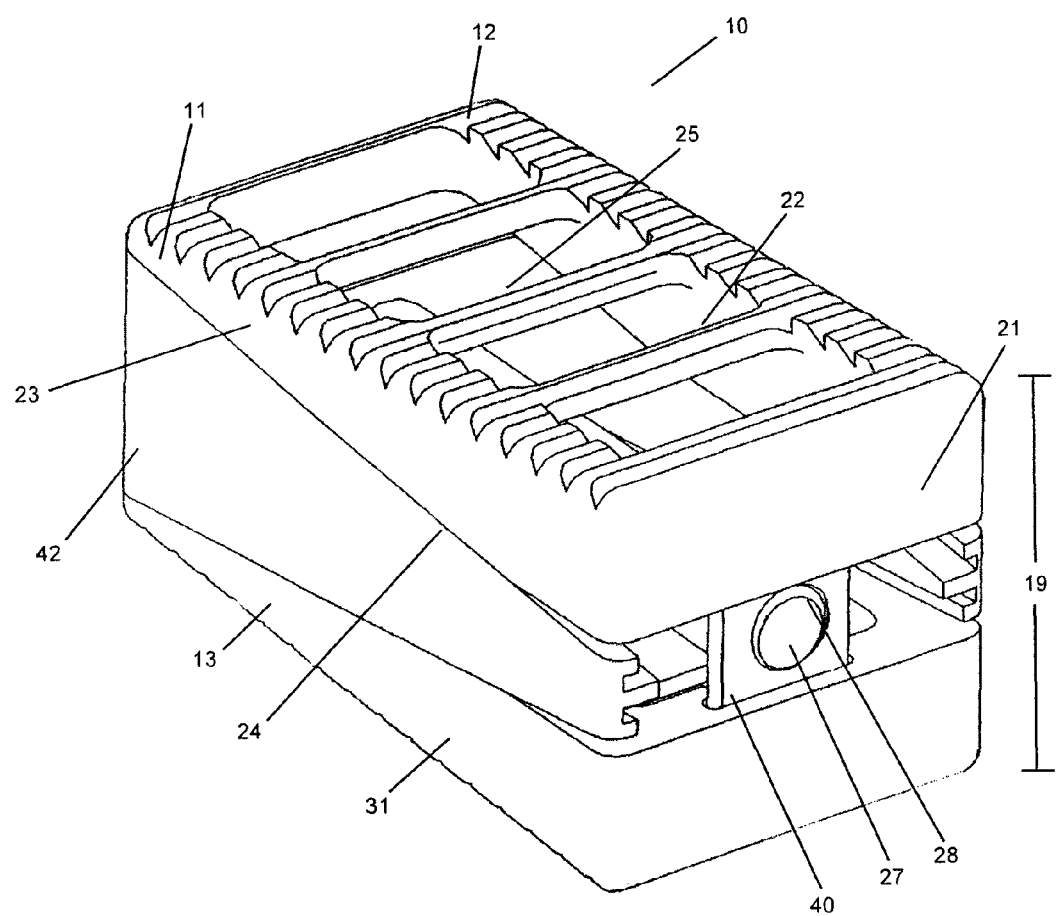
FIG. 2 is a perspective of the spinal fusion device of this invention in the deployed mode.

The device 10 has two extreme positions and is adjustable infinitely between those positions, eg., in the insertion mode, the extended position of the leading end of the structure has a height 20 approximately the same as the height of the sections and a length approximately twice the length of one section, as shown in FIG. 1. In the increased height mode, the expanded position, shown in FIG. 2, the height 19 is the sum of the height of the individual sections with the distractor 42 and the length is approximately the same as the length of a section.

The fusion device 10 may be made of conventional materials used for surgical implants, such as stainless steel and its many different alloys, titanium, and any other metal with the requisite strength and biologically inert properties. Polymeric materials with adequate strength and biological properties may also be used in the construction of the fusion device.

The upper section 11 is formed with an end wall 21 a top surface 12 and depending sidewalls 22 and 23. The sidewalls terminate in an inclined plane 24 which extends from the end wall 21 to the top surface 12. The top surface 12 has a large aperture 25 therethrough to provide for bone ingrowth. The top surface 12 has a narrower groove 26 extending along the sidewalls 22 and 23. The groove 26 engages the flange 43 of distractor 42 to guide the relative movement of the sections maintaining the distractor 42 and the depending sidewalls in alignment. The link 40 has a bore 27 with internal threads 28 to cooperate with the threads 41 on the link 40.

The bottom surface 14 of the lower section 13 has a large aperture 30, as shown in FIG. 1, to facilitate bone ingrowth after implantation. The lower section 13 is a U-shaped channel with opposed upstanding sidewalls 31 and 32 projecting from the bottom surface. The side walls 31 and 32 have a short end 33 and a long end 34. The sidewalls 31 and 32 terminate in an inclined plane extending from the short end 33 toward the long end 34. The upstanding walls each have a groove 35 along the edge of the inclined plane. The movement of the flange 44 through the groove 35 contributes to the alignment of the distractor 42 and lower section as they move relative to each other.

The ends of the inclined planes of the upstanding and depending walls are smooth ramps to provide ease in the relative sliding contact between the distractor and upper and lower section surfaces. Other embodiments of the complementary surfaces may provide additional or substitute guidance to maintain the upper and lower sections in alignment during movement of the contacting surfaces of the inclined planes, such as, the ends of the inclined planes may be sloped across the thickness of the side walls or a stepped ramp may be used.

Figure 3:
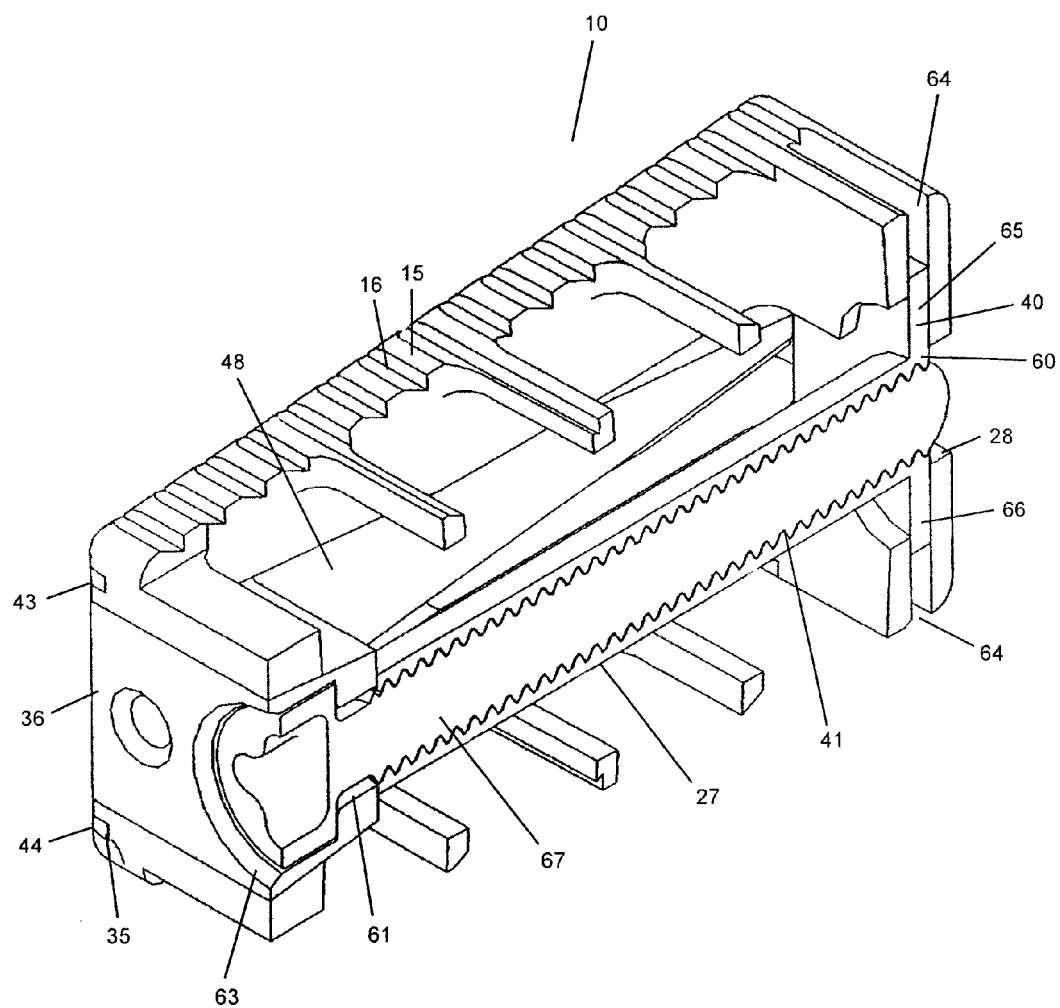
FIG. 3 is a side view, partially in section, of the implant of FIG. 2.

The ramp or distractor 42 is dimensioned to be inserted into the trailing end of the interior cavity between the upper section and the lower section of the spinal infusion device 10, as shown in FIG. 1. An end wall 36 is dimensioned to close the opening formed in the trailing end between the upper section 11 and the lower section 13 by the depending and upstanding sidewalls. The upper surface of the plug has an inclined ramp on each side to accommodate the inclined plane 24 of the depending walls 22 and 23 of the upper section. The end wall 36 has a larger circumferential end dimensioned to extend to the outer periphery of the upper and lower sections to make a smooth trailing end outer surface. Extending from the end wall 36 into the cavity of the hollow structure 10 is the body 47 of the distractor 42. The body is connected to the end wall 36 by two rails 48 and 49 leaving the central area open for bone ingrowth. The end plug 36 has a bore 61 aligned with bore 60 in link 40. The bore 61 has a larger countersunk bore 63 in the end wall 36. These bores are aligned with the threaded tube 29 attached to the link 40, as shown in FIG. 3.

The leading ends of the upper and lower sections are formed with a vertical slot 64. Link 40 includes an upper flange 65 and a lower flange 66 of a size and shape to slide within the vertical slot 64 as the distractor 42 moves into the central cavity foreshortening the implant and increasing the distance between the leading ends of the sections. The threaded tube 29 surrounds the bore 60 and extends toward the bore 61. A jack screw 67 is inserted through bore 61 engaging the threads in the tube 27. As the jack screw 67 is tightened, the ramp is drawn toward the leading end of the implant and the leading ends of the upper and lower sections slide apart along flanges 65 and 66.

The spinal fusion device is inserted in the disk space between adjacent vertebrae in the extended position with the top surface in contact with the end plate of one vertebra and the bottom surface in contact with the end plate of an adjacent vertebra. The surgeon turns the jack screw 67 causing the upper and lower sections to move along the complementary inclined plane to shorten the fusion device and increase the distance between the end plates of the adjacent vertebrae. The adjustment may continue until the optimum distance between vertebrae has been reached. At this time, the jack screw may be removed and replaced by a bolt (not shown) of sufficient length to retain the upper and lower sections together.

Figure 4:
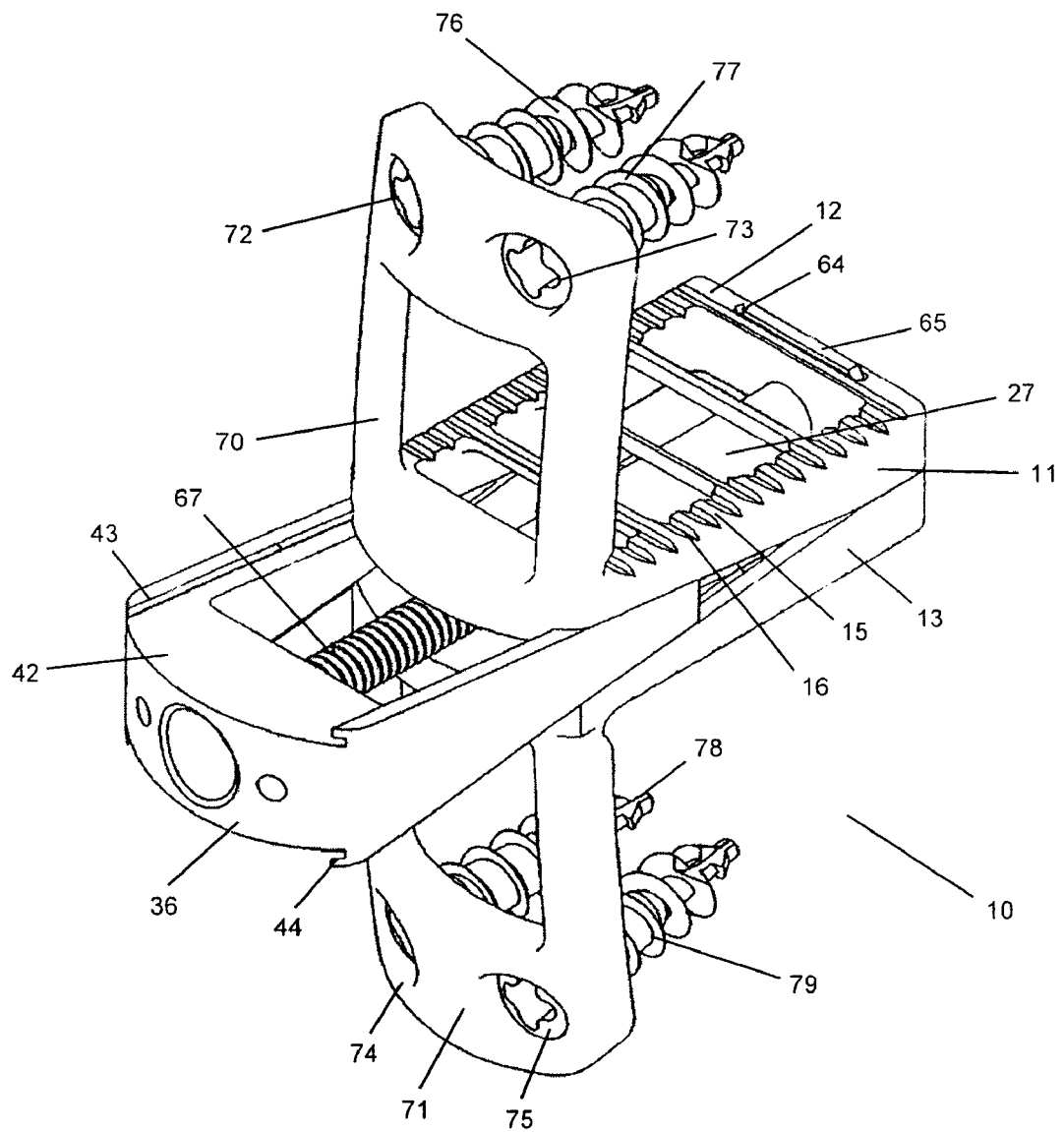
FIG. 4 is an end view in perspective another embodiment of the implant of this invention in the thin mode.
Figure 5:
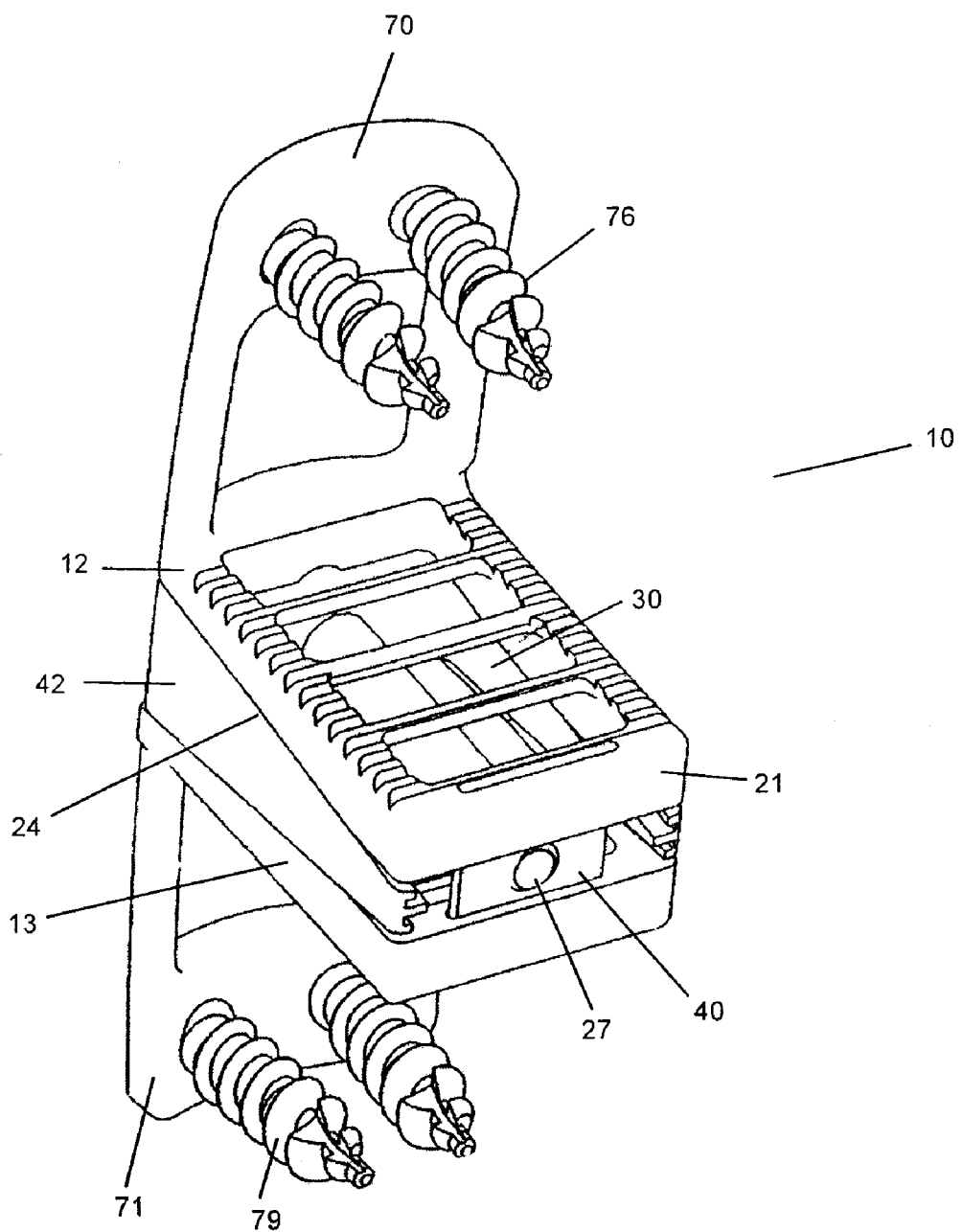
FIG. 5 is a perspective of the spinal fusion device of FIG. 4 of this invention in the deployed mode.
Figure 6:
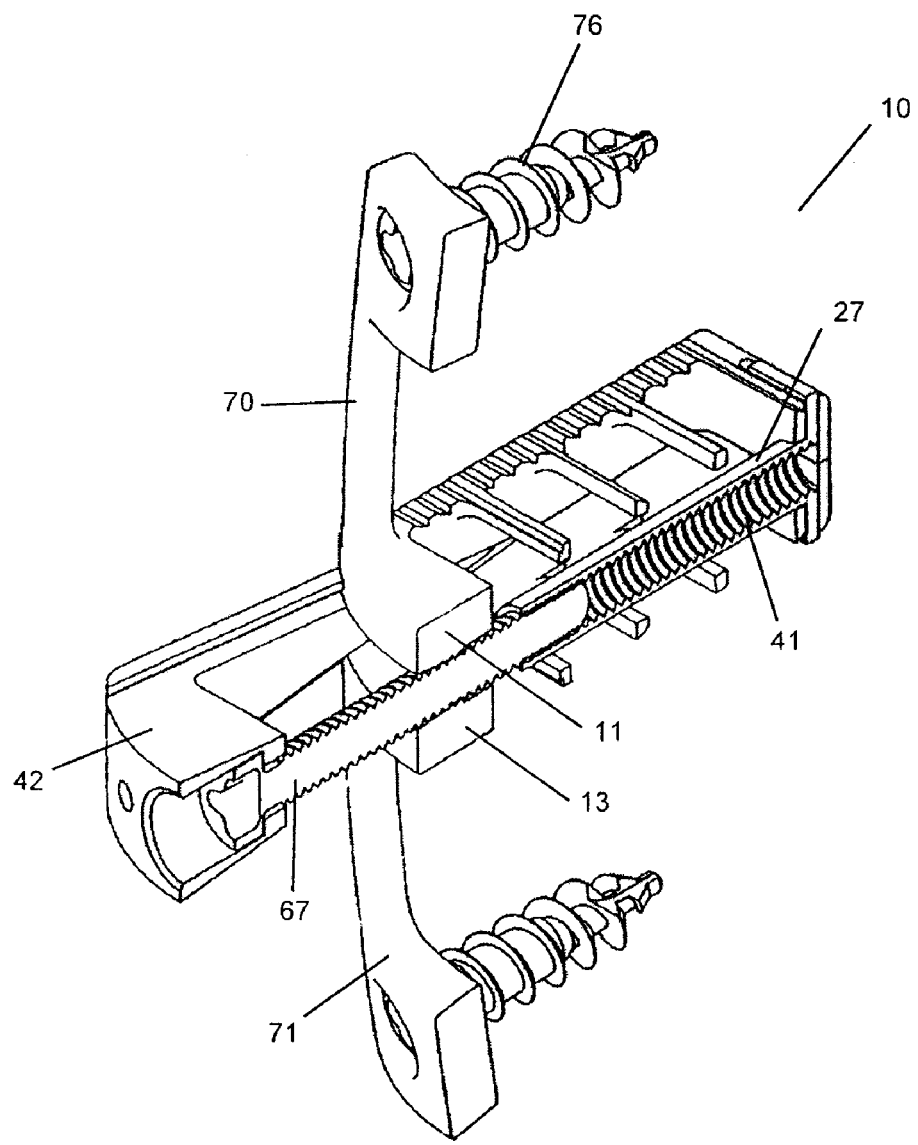
FIG. 6 is a side view, partially in section, of the implant of FIG. 4.

In FIGS. 4, 5 and 6, another embodiment of the implant 10 is illustrated with integral brackets on the upper and lower sections for engaging adjacent vertebrae. Each bracket has apertures therethrough for placing bone screws into the adjacent vertebra. The bone screws add stability to the implant and provide additional security to prevent dislodgement of th implant under normal activity.

The upper section has a bracket 70 attached to the trailing end wall. As shown, the bracket extends normal to the top surface 12 in a direction away from the distractor 42. The lower section 13 has a bracket 71 attached to the trailing end wall and extending in the opposite direction from the lower section. Each bracket 70, 71 is shown with countersunk apertures 72, 73, 74 and 75. Bone screws 76, 77, 78 and 79 are inserted into the apertures and threaded into the vertebrae.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A spinal fusion device for placement in the disk space between adjacent vertebrae comprising a hollow body having an upper section with a top surface for contacting one vertebra and a lower section with a bottom surface for contacting the adjacent vertebra, said top surface and said bottom surface having means for engaging adjacent vertebrae, depending sidewalls extending from said top surface terminating in a first inclined plane, upstanding sidewalls projecting from said bottom surface terminating in a second inclined plane, said upper section having a first end wall, said lower section having a second end wall, said first end wall including a first slot and said second end wall including a second slot, a link having a first end slidably mounted in said first slot and a second end slidably mounted within said second slot, whereby said link is slidably mounted in said first end wall and said second end wall and said upper section and said lower section may move apart.

2. A spinal fusion device of claim 1 wherein a distractor is slidably disposed between said depending sidewalls and said upstanding sidewalls, said depending sidewalls and said upstanding sidewalls in sliding contact with said distractor along said first inclined plane and said second inclined plane whereby the distance between said bottom surface and said top surface is adjustable by moving said upper section relative to said lower section.

3. A spinal fusion device of claim 2 wherein said link includes a tube with internal threads, said distractor includes a bore, a jack screw in said bore threaded into said tube whereby said distractor moves relative to said upper section and said lower section as said jack screw is threaded into said tube.

4. A spinal fusion device of claim 2 wherein said upstanding walls have a second groove along said second inclined plane, a second flange connected to said distractor, said second flange adapted to contact said portion of said second groove and provide alignment of said upper section and said lower section.

5. A spinal fusion device of claim 4 wherein said depending walls have a groove along said first inclined plane, a flange connected to said distractor, said flange adapted to contact said portion of said groove and provide alignment of said upper section and said lower section.

6. A spinal fusion device of claim 2 wherein said depending walls have a groove along said first inclined plane, a flange connected to said distractor, said flange adapted to contact said portion of said groove and provide alignment of said upper section and said lower section.

7. A spinal fusion device of claim 1 wherein said means for engaging a vertebra is a series of lands and grooves on said top surface.

8. A spinal fusion device of claim 7 wherein said means for engaging a vertebra is a series of lands and grooves on said bottom surface.

9. A spinal fusion device of claim 8 wherein said means for engaging a vertebra is a bracket on said bottom surface.

10. A spinal fusion device of claim 9 wherein said means for engaging a vertebra is a bracket on said top surface.

11. A spinal fusion device of claim 1 wherein said means for engaging a vertebra is a bracket on said top surface.

12. A spinal fusion device of claim 1 wherein said means for engaging a vertebra is a bracket on said bottom surface.

* * * * *